United States Patent [19]
Takinami et al.

[11] 3,971,701
[45] July 27, 1976

[54] METHOD FOR PRODUCING L-GLUTAMIC ACID BY FERMENTATION

[75] Inventors: Koichi Takinami, Yokohama; Takashi Tanaka, Kawasaki; Michiaki Chiba, Yokohama; Yoshio Hirose, Fujisawa, all of Japan

[73] Assignee: Ajinomoto Co., Inc., Tokyo, Japan

[22] Filed: Oct. 7, 1974

[21] Appl. No.: 512,480

[30] Foreign Application Priority Data
Oct. 17, 1973 Japan............................ 48-116666

[52] U.S. Cl.................................... 195/47; 195/79; 195/96; 195/112; 195/114
[51] Int. Cl.² .................... C12D 13/06; C12K 1/02; C12B 1/20
[58] Field of Search ............... 195/96, 47, 112, 79, 195/29, 114

[56] References Cited
UNITED STATES PATENTS 3,164,531  1/1965  Okada et al. .......................... 195/47
3,399,114  8/1968  Ohsawa .............................. 195/114

FOREIGN PATENTS OR APPLICATIONS
7,200,673  10/1972  Japan ................................. 195/47

OTHER PUBLICATIONS
Chem. Abstracts 73:97360K.
Nakayama et al., "Induction of Nutritional Mutants of Glutamic Acid Bacteria and Their Amino Acid Accumulation", J. Gen. Appl. Microbiol., vol. 7, No. 1 (1961), pp. 41–51.

Primary Examiner—A. Louis Monacell
Assistant Examiner—Thomas G. Wiseman
Attorney, Agent, or Firm—Hans Berman; Kurt Kelman

[57] ABSTRACT

Mutants of glutamic acid producing strains of Brevibacterium which are more sensitive to N-palmitoylglutamic acid than the parent strains require less surfactant to suppress excessive biotin activity in a fermentation medium for permitting glutamic acid production and correspondingly less antifoaming agent without loss of glutamic acid yield.

5 Claims, No Drawings

METHOD FOR PRODUCING L-GLUTAMIC ACID BY FERMENTATION

This invention relates to a method for producing L-glutamic acid, particularly to a method for producing L-glutamic acid in a medium which contains much biotin.

L-Glutamic acid (hereinafter referred to as glutamic acid) is useful as a seasoning, and has been produced by fermentation.

In the fermentation of a culture medium containing much biotin, addition of a surfactant was necessary heretofore for suppressing the excessive biotin activity (U.S. Pat. No. 3,164,531).

However, the surfactant involves a significant rise in the cost of the glutamic acid. Furthermore, the medium containing a surfactant foams vigorously, and a larger amount of defoaming agent is necessary.

From a glutamic acid producing microorganism of Brevibacterium there have now been induced mutants sensitive to N-palmitoyl glutamic acid, which, when cultured in a medium containing an excessive amount of biotin, permit the amount of surfactant necessary for suppressing the excessive biotin to be greatly reduced without decreasing the yield of glutamic acid.

The mutants of this invention are more sensitive to N-palmitoyl glutamic acid than the parent strain. They include

*Brevibacterium flavum* AJ 3612 (FERM-P 2308) and
*Brevibacterium lactofermentum* AJ 3611 (FERM-P 2307).

They were deposited with the Fermentation Research Institute, Agency of Industrial Science and Technology, at Inage-Higashi, Chiba-shi, Japan, and are available from the Fermentation Research Institute.

The mutuants were induced from B. flavum ATCC 14067 and B. lactofermentum ATCC 13869 respectively. The following glutamic acid producing microorganisms can be used also as the parent strains:

*Brevibacterium divaricatum* NRRL B-2311
*Brevibacterium saccharoliticum* ATCC 14066, and
*Brevibacterium roseum* ATCC 13825

The method of mutation is conventional such as exposure of the parent strain to gamma-rays, X-rays, or ultra-violet light, or to chemical mutagenic agents such as N-methyl-N'-nitro-N-nitrosoguanidine. The mutants mentioned above were induced by exposure to 250 γ/ml N-methyl-N'-nitro-N-nitrosoguanidine at 30°C for 30 minutes.

Usually, the mutant sensitive to N-palmitoyl glutamic acid is also sensitive to the following compounds:

Fatty acids having 6 to 19 straight carbon chains or their salts: lauric acid, myristic acid, stearic acid, palmitic acid and so on.

Esters of the fatty acids: esters of glycerol, sorbitan, sucrose, polyethyleneglycol, polyethylenepolypropyleneglycol, polyoxyethylene sorbitan ether or polyoxyethylenepolyoxypropylene sorbitan ether.

N-Acyl derivatives of α-amino acids in which acyl is the acyl group of the fatty acids, the amino acids being, glycine, alanine, valine, leucine, threonine, serine, aspartic acid, glutamic acid, ornithine, lysine, arginine, phenylalanine, tyrosine, tryptophan, methionine or other α-amino acids.

The mutant sensitive to N-palmitoyl glutamic acid can be distinguished from the parent strain by a "disk method". That is, a disk of filter paper which was previously dipped in a solution containing N-palmitoylglutamic acid is placed in an agar-plate, on which the tested microorganism is being cultured. A sensitive strain does not grow on the fringe of the disk, while an insensitive strain grows around a disk containing an amount of N-palmitoylglutamic acid which inhibits the sensitive strain.

The mutant exhibits its superiority when it is cultured in aqueous culture media which contain too much biotin for the production of glutamic acid, such as, those which contain beet molasses, cane molasses, fruit juice, raw sugar and starch hydrolyzate as a carbon source.

The media of this invention, therefore, contain too much biotin for glutamic acid production in the absence of surfactants, and other conventional ingredients such as a carbon source, a nitrogen source, inorganic ions, and minor organic nutrients.

The surfactants added to the media to suppress excessive activity of biotin are the same as those to which the mutants are sensitive, and are fatty acids having straight chains or compounds containing moieties of the fatty acids.

The following compounds are most suitable surfactants:

lauric acid, myristic acid, palmitic acid, stearic acid, margaric acid polyethyleneglycol-mono-palmitate
polyethyleneglycol-mono-margarate polyethyleneglycol-polypropyleneglycol-mono-palmitate polyoxyethylenesorbitan-mono-laurate
polyoxyethylenesorbitan-mono-myristate
polyoxyethylenesorbitan-mono-palmitate
polyoxyethylenesorbitan-mono-stearate
polyoxyethylene-polyoxypropylene-sorbitan-mono-palmitate glycerol-mono-palmitate sorbitan-mono-palmitate sucrose-mono-palmitate, sucrose-mono-stearate N-palmitoyl-glycine
N-palmitoyl-alanine
N-palmitoyl-valine
N-palmitoyl-leucine
N-palmitoyl-threonine
N-palmitoyl-phenylalanine
N-palmitoyl-aspartic acid
N-palmitoyl-glutamic acid
N-palmitoyl-methionine
N-palmitoyl-tyrosine
N-palmitoyl-tryptophan
N-myristoyl-glutamic acid
N-stearoyl-glutamic acid N,N'-dipalmitoyl-ornithine
N,N'-dipalmitoyl-lysine The amount of surfactant added to the medium is usually less than 0.2 g/dl, and is one half or one quarter of the amount of surfactant employed in the known method. The surfactant is added to the medium prior to starting the cultivation or during the logarithmic phase of growth.

Cultivation is aerobically carried out preferably maintaining pH of medium at 6 to 9, and the temperature at 30° to 40°C.

The yield of glutamic acid is superior to the known process, and, the amount of defoaming agent necessary in the instant process is smaller than in the known process.

EXAMPLE 1

An agar medium was prepared to contain per deciliter, 1 g yeast extract, 1 g peptone, 0.5 g NaCl and 2 g agar, adjusted to pH 7.0, placed in Petri-dishes, and sterilized with steam. $5 \times 10^5$ Cells of *B. lactofermentum* AJ 3611, its parent strain ATCC 13869, *B. flavum* AJ 3612 and its parent strain ATCC 14067 were inoculated on the agar medium in respective dishes.

Filter paper disks were dipped in a solution containing the amount of N-palmitoylglutamic acid shown in Table 1, dried, and placed on the agar medium.

The Petri-dishes were incubated at 30°C for 16 – 48 hours. The formation of a halo around the disk was observed.

EXAMPLE 2

In a method as described in Example 1, filter paper disks were dipped in a solution containing the compounds shown in Table 2 in the amounts also shown in Table 2. *B. lactofermentum* ATCC 13869 and *B. lactofermentum* AJ 3611 were cultured in the same manner as in Example 1. Growth of the strains (formation of halo) was observed and the results are shown in Table 2.

EXAMPLE 3

An aqueous culture medium was prepared to contain, per milliliter, 100 mg cane molasses (as glucose), 1 mg $KH_2PO_4$, 1 mg $MgSO_4.7$ aq, and 0.10 μg thiamine.HCl, and 30 ml batches of the culture medium were placed in 500 ml flasks, and heated at 115°C for 10 minutes.

Brevibacterium lactofermentum AJ 3611, and ATCC 13869 were inoculated in the aqueous culture medium and cultured at 31.5°C with shaking. The pH of the medium was maintained within the range from 6.5 to 8.0 by feeding 40% urea solution.

When the optical density at 562 mμ of each culture medium diluted 26 times reached 0.30, polyoxyethylene-sorbitan-monopalmitate was added in the amounts as shown in Table 3.

After 30 hours cultivation, the amounts of glutamic acid shown in Table 3 were found in the culture broths.

EXAMPLE 4

In the method described in Example 3, polyoxyethylene-sorbitan-mono-stearate was used in place of polyoxyethylene-sorbitan-mono-palmitate. The results are shown in Table 4.

EXAMPLE 5

Cane molasses in the aqueous culture medium of Example 3 was replaced by 32 mg/ml beet molasses (as glucose), and 300 ml batches of the aqueous culture medium were placed in 1 liter jar-fermenters and heated with steam.

B. lactofermentum AJ 3611 and ATCC 13869 were cultured at 31.5°C with aerating and agitating. The pH of the medium was maintained at 7.8 by feeding gaseous ammonia.

When the optical density of the culture medium diluted 26 times reached 0.30, 0.02 mg/ml and 0.03 mg/ml polyoxyethylene-sorbitan-mono-palmitate were added to the culture media of AJ 3611 and ATCC 13869, respectively.

After 24 hours cultivation, 21 mg/ml glutamic acid was found in the culture broth of AJ 3611, and 19 mg/ml glutamic acid in the culture broth of ATCC 13869.

EXAMPLE 6

In the manner described in Example 3, B. flavum AJ 3612 and ATCC 14067 were cultured. 2 Mg/ml polyoxyethylene-sorbitan-mono-palmitate was added to the culture medium of AJ 3612, and 3 mg/ml to the culture medium of ATCC 14067.

AJ 3612 accumulated 52 mg/ml glutamic acid in the culture broth, while ATCC 14067 accumulated 50 mg/ml glutamic acid.

EXAMPLE 7

B. lactofermentum AJ 3611 and ATCC 13869 were cultured at 31.5°C for 16 hours in an aqueous culture medium containing per milliliter 36 mg glucose, 1 mg $KH_2PO_4$, 1 mg $MgSO_4.7$ aq, 10 μg $FeSO_4.7$ aq, 8 μg $MnSO_4.4$ aq, 0.10 μg thiamine.HCl, 0.24 mg soyprotein hydrolyzate (as nitrogen), 0.05 μg biotin and 10 mg urea.

A fermentation medium of the same composition, but not containing biotin was also prepared and 20 ml batches of the medium were placed in 500 ml flasks.

Four mililiters of the culture broths of AJ 3611 and ATCC 13869 were transferred to the 500 ml flasks. Cultivation was carried out at 31.5°C for 24 hours. Surfactants were added to the medium after 6 hours of cultivation.

The resulting yields of glutamic acid are listed in Table 5.

Table 1

| Amount of N-palmitoylglutamic acid contained in the solution in which the disks were dipped (mg/dl) | Growth | | | |
|---|---|---|---|---|
| | AJ 3611 | ATCC 13869 | AJ 3612 | ATCC 14067 |
| 30 | + | + | + | + |
| 60 | + | + | + | + |
| 80 | − | + | − | + |
| 100 | − | + | − | + |
| 120 | − | + | − | − |
| 160 | − | − | − | − |
| 200 | − | − | − | − |
| 400 | − | − | − | − |

Symbol + indicates that a halo was not observed and growth was observed, and symbol − indicates that a halo was observed and growth was not observed.

Table 2

| Amount of fatty acid in the solution in which disks were dipped (mg/dl) | | Growth | |
|---|---|---|---|
| | | B. lactofermentum AJ 3611 | B. lactofermentum ATCC 13869 |
| lauric acid | 0 | + | + |
| | 50 | + | + |
| | 100 | − | + |
| | 150 | − | + |
| | 200 | − | − |
| myristic acid | 0 | + | + |
| | 50 | + | + |

Table 2-continued

| Amount of fatty acid in the solution in which disks were dipped (mg/dl) | | Growth B. lactofermentum AJ 3611 | B. lactofermentum ATCC 13869 |
|---|---|---|---|
| palmitic acid | 100 | + | + |
|  | 150 | − | + |
|  | 200 | − | − |
|  | 0 | + | + |
|  | 50 | + | + |
|  | 100 | + | + |
|  | 150 | − | + |
|  | 200 | − | + |
| stearic acid | 0 | + | + |
|  | 50 | + | + |
|  | 100 | + | + |
|  | 150 | + | + |
|  | 200 | − | + |
| N-palmitoyl valine | 0 | + | + |
|  | 50 | + | + |
|  | 100 | − | + |
|  | 125 | − | + |
|  | 150 | − | − |
| N-palmitoyl alanine | 0 | + | + |
|  | 50 | + | + |
|  | 100 | − | + |
|  | 125 | − | + |
|  | 500 | − | − |
| polyoxyethylene-sorbitan-mono-palmitate | 0 | + | + |
|  | 30 | + | + |
|  | 60 | − | + |
|  | 90 | − | + |
|  | 120 | − | − |
| sorbitan-monostearate | 0 | + | + |
|  | 1000 | + | + |
|  | 2000 | + | + |
|  | 3000 | − | + |
|  | 4000 | − | − |

Table 3

| Polyoxyethylene-sorbitan-mono-palmitate added (mg/ml) | Yield of glutamic acid (%) | |
|---|---|---|
|  | AJ 3611 | ATCC 13869 |
| 0 | 1.1 | 2.3 |
| 0.5 | 27.5 | 6.1 |
| 1.0 | 44.5 | 22.5 |
| 2.0 | 55.0 | 40.1 |
| 4.0 | 53.1 | 52.0 |

Table 4

| Polyoxyethylene-sorbitan-mono-stearate added (mg/ml) | Yield of glutamic acid (%) | |
|---|---|---|
|  | AJ 3611 | ATCC 13869 |
| 0 | 3.3 | 2.6 |
| 1.0 | 28.0 | 5.5 |
| 2.0 | 45.9 | 24.4 |
| 3.0 | 50.6 | 38.8 |
| 4.0 | 52.1 | 45.1 |

Table 5

| Surfactant added | AJ 3611 Amount of surfactant (mg/ml) | AJ 3611 Yield of glutamic acid (%) | ATCC 13869 Amount of surfactant (mg/ml) | ATCC 13869 Yield of glutamic acid (%) |
|---|---|---|---|---|
| Glycerol-mono-palmitate | 6.0 | 20 | 10 | 17 |
| Sorbitan-mono-palmitate | 3.0 | 33 | 5.0 | 32 |
| Sucrose-mono-palmitate | 1.0 | 51 | 2.0 | 43 |
| Polyethyleneglycol-mono-palmitate | 1.0 | 54 | 2.0 | 51 |
| Polyethyleneglycol-polypropyleneglycol-mono-palmitate | 1.0 | 49 | 2.0 | 47 |
| Lauric acid | 0.3 | 30 | 0.4 | 28 |
| Myristic acid | 0.3 | 40 | 0.4 | 40 |
| Palmitic acid | 0.2 | 44 | 0.3 | 38 |
| Margaric acid | 0.2 | 43 | 0.3 | 41 |
| Stearic acid | 0.3 | 35 | 0.4 | 29 |
| Sucrose-mono-stearate | 0.3 | 53 | 0.5 | 46 |
| Polyethyleneglycol-mono-margarate | 0.5 | 57 | 1.0 | 52 |
| N-palmitoylglycine | 0.07 | 52 | 0.1 | 50 |
| N-palmitoylalanine | 0.07 | 55 | 0.1 | 51 |
| N-palmitoylvaline | 0.07 | 50 | 0.1 | 50 |
| N-palmitoylleucine | 0.07 | 45 | 0.1 | 44 |
| N-palmitoylthreonine | 0.15 | 48 | 0.2 | 48 |
| N-palmitoylphenylalanine | 0.04 | 49 | 0.05 | 46 |
| N-palmitoyl aspartic acid | 0.03 | 53 | 0.05 | 48 |
| N-palmitoyl glutamic acid | 0.05 | 57 | 0.1 | 51 |
| N-myristoyl glutamic acid | 0.07 | 57 | 0.1 | 50 |
| N-stearoyl glutamic acid | 0.07 | 48 | 0.1 | 45 |
| N,N'-dipalmitoyl ornithine | 0.5 | 50 | 1.0 | 40 |
| N,N'-dipalmitoyl lysine | 0.5 | 50 | 1.0 | 48 |
| N-palmitoyl methionine | 0.07 | 46 | 0.1 | 46 |
| N-palmitoyl tyrosine | 0.04 | 45 | 0.05 | 43 |
| N-palmitoyl tryptophan | 0.04 | 45 | 0.05 | 44 |
| None | — | 1 | — | 3 |

What is claimed is:

1. A method of producing L-glutamic acid which comprises:
    a. culturing an L-glutamic acid producing microorganism in an aqueous culture medium until glutamic acid accumulates in said medium,
        1. said medium containing assimilable sources of carbon and nitrogen, inorganic ions and minor organic nutrients necessary for the growth of said microorganisms, a surfactant, and an amount of biotin too great to permit significant production of glutamic acid by the cultured microorganism in the absence of said surfactant,
        2. said microorganism being a mutant derived from an L-glutamic acid producing parent strain of Brevibacterium, 3. said mutant being more sensitive to N-palmitoyl-glutamic acid than said parent strain, and
4. said surfactant being a fatty acid having a straight chain of 6 to 19 carbon atoms, a salt of said fatty acid, an ester of said fatty acid, or an N-acyl-α-amino acid, the acyl group in said N-acyl-α-amino acid being the acyl radical of said fatty acid; and b. recovering the accumulated glutamic acid from said medium.

2. A method as set forth in claim 1 wherein said microorganism is *Brevibacterium flavum* FERM-P 2308 or *Brevibacterium lactofermentum* FERM-P 2307.

3. A method as set forth in claim 1, wherein said surfactant is polyethyleneglycol-mono-palmitate, polyethyleneglycol-mono-margarate, polyoxyethylene-sorbitan-mono-palmitate or polyoxyethylene-sorbitan-mono-stearate.

4. A method as set forth in claim 1, wherein said medium contains beet molasses or cane molasses as said carbon source.

5. A method as set forth in claim 1, wherein said amount of surfactant is less than 0.2 g/dl.

* * * * *